United States Patent
Goto

(10) Patent No.: US 11,390,812 B2
(45) Date of Patent: Jul. 19, 2022

(54) COMPOUND, COMPOSITION, CURED OBJECT, OPTICALLY ANISOTROPIC BODY, AND REFLECTIVE FILM

(71) Applicant: FUJIFILM Corporation, Tokyo (JP)

(72) Inventor: Ryoji Goto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 29 days.

(21) Appl. No.: 17/026,289

(22) Filed: Sep. 20, 2020

(65) Prior Publication Data

US 2021/0002556 A1 Jan. 7, 2021

Related U.S. Application Data

(63) Continuation of application No. PCT/JP2019/012149, filed on Mar. 22, 2019.

(30) Foreign Application Priority Data

Mar. 23, 2018 (JP) .............................. JP2018-057225

(51) Int. Cl.
- *G02B 1/08* (2006.01)
- *C09K 19/38* (2006.01)
- *C07C 69/54* (2006.01)

(52) U.S. Cl.
CPC .......... *C09K 19/3852* (2013.01); *C07C 69/54* (2013.01); *G02B 1/08* (2013.01); *C09K 2323/03* (2020.08); *C09K 2323/031* (2020.08); *C09K 2323/033* (2020.08)

(58) Field of Classification Search
CPC ........ C09K 19/3852; C09K 2019/0448; C09K 2323/03; C09K 2323/031; C09K 2323/033; C07C 69/54; G02B 1/08; G02B 5/3016
USPC ...... 428/1.3, 1.31, 1.33; 252/299.6; 349/119
See application file for complete search history.

(56) References Cited

U.S. PATENT DOCUMENTS

| 2015/0376505 A1 | 12/2015 | Gotoh et al. |
| 2017/0107427 A1 | 4/2017 | Takahashi et al. |
| 2019/0177268 A1 | 6/2019 | Fukushima et al. |

FOREIGN PATENT DOCUMENTS

| JP | 2005015406 | 1/2005 |
| JP | 2013014538 | 1/2013 |
| JP | 2016011347 | 1/2016 |
| WO | 2015190399 | 12/2015 |
| WO | 2018034216 | 2/2018 |

OTHER PUBLICATIONS

"International Search Report (Form PCT/ISA/210) of PCT/JP2019/012149," dated Apr. 23, 2019, with English translation thereof, pp. 1-5.
"Written Opinion of the International Searching Authority (Form PCT/ISA/237) of PCT/JP2019/012149," dated Apr. 23, 2019, with English translation thereof, pp. 1-11.
"Office Action of Japan Counterpart Application" with English translation thereof, dated Aug. 31, 2021, p. 1-p. 10.

*Primary Examiner* — Ruiyun Zhang
(74) *Attorney, Agent, or Firm* — JCIPRNET

(57) ABSTRACT

The present invention provides a compound by which high refractive index anisotropy Δn and inhibition of colorability can be compatible. The present invention further provides a composition including the above-mentioned compound, a cured object, an optically anisotropic body, and a reflective film. The compound of the present invention is represented by General Formula (1).

General Formula (I)

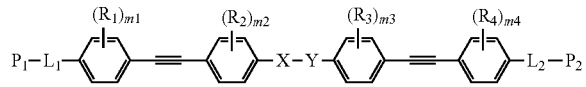

18 Claims, No Drawings

COMPOUND, COMPOSITION, CURED OBJECT, OPTICALLY ANISOTROPIC BODY, AND REFLECTIVE FILM

CROSS-REFERENCE TO RELATED APPLICATIONS

This application is a Continuation of PCT International Application No. PCT/JP2019/012149 filed on Mar. 22, 2019, which claims priority under 35 U.S.C. § 119(a) to Japanese Patent Application No. 2018-057225 filed on Mar. 23, 2018. Each of the above applications is hereby expressly incorporated by reference, in its entirety, into the present application.

BACKGROUND OF THE INVENTION

1. Field of the Invention

The present invention relates to a compound, a composition, a cured object, an optically anisotropic body, and a reflective film.

2. Description of the Related Art

A liquid crystal compound can be applied to various usage applications. For example, the liquid crystal compound is applied to manufacture of an optically anisotropic body typified by a retardation film, or to manufacture of a reflective film obtained by fixing a cholesteric phase.

In order to reduce a thickness of the optically anisotropic body and cholesteric reflective film, it is required to improve refractive index anisotropy $\Delta n$ (hereinafter also simply referred to as $\Delta n$) of the liquid crystal compound.

For example, JP2005-015406A discloses a compound to which a tolan skeleton is linked as a compound having high $\Delta n$.

SUMMARY OF THE INVENTION

Meanwhile, in a case of increasing $\Delta n$, in general, there are many cases having a problem of coloration associated with an increase in wavelength. The problem is particularly remarkable in a case where a relatively thick film such as a cholesteric reflective film is required.

An object of the present invention is to provide a compound (liquid crystal compound) by which high refractive index anisotropy $\Delta n$ and inhibition of colorability can be compatible.

Another object of the present invention is to provide a composition including the above-mentioned compound, a cured object, an optically anisotropic body, and a reflective film.

As a result of intensive studies, the inventors of the present invention have found that the above-described objects can be achieved by the following configuration. They also have found that, in a case where the following configuration is adopted, and in a case where the compound of the present invention is used as a liquid crystal compound, light fastness is also improved.

[1] A compound represented by General Formula (1).
[2] The compound according to [1], in which Y represents —C($R_{ya}$)($R_{yb}$)— in General Formula (1).
[3] The compound according to [1] or [2], in which at least one of $m_1$, $m_2$, $m_3$, or $m_4$ represents an integer of 1 or greater in General Formula (1).
[4] The compound according to any one of [1] to [3], in which, in General Formula (1), at least one of $m_1$, $m_2$, $m_3$, or $m_4$ represents an integer of 1 or greater,
at least one of $R_1$, $R_2$, $R_3$, or $R_4$ respectively matched with $m_1$, $m_2$, $m_3$, or $m_4$ each representing an integer of 1 or greater is an alkyloxycarbonyl group having 1 to 20 carbon atoms or an alkylaminocarbonyl group having 1 to 20 carbon atoms,
one or more methylene groups in an alkyl group moiety in the alkyloxycarbonyl group and the alkylaminocarbonyl group each independently may be substituted by —O— or —C(=O)—, and
the alkyl group moiety may have a fluorine atom.
[5] The compound according to any one of [1] to [4], in which, in General Formula (1), $L_1$ represents a group represented by Formula (A), and $L_2$ represents a group represented by Formula (B).
[6] A composition comprising the compound according to any one of [1] to [5].
[7] The composition according to [6], further comprising a polymerization initiator.
[8] The composition according to [6] or [7], further comprising a chiral agent.
[9] A cured object obtained by curing the composition according to any one of [6] to [8].
[10] An optically anisotropic body obtained by curing the composition according to any one of [6] to [8].
[11] A reflective film obtained by curing the composition according to any one of [6] to [8].

According to the present invention, it is possible to provide a compound by which high refractive index anisotropy $\Delta n$ and inhibition of colorability can be compatible.

According to the present invention, it is also possible to provide a composition including the above-mentioned compound, a cured object, an optically anisotropic body, and a reflective film.

DESCRIPTION OF THE PREFERRED EMBODIMENTS

Hereinafter, the present invention will be described in detail. In the present specification, a numerical range represented using "to" means a range including numerical values described before and after the preposition "to" as a lower limit value and an upper limit value.

In addition, in the present specification, a "(meth)acryloyloxy group" is a description representing both an acryloyloxy group and a methacryloyloxy group.

In the indication of a group (atomic group) in the present specification, the indication not including substitution or unsubstitution includes groups having a substituent and also groups not having a substituent. For example, an "alkyl group" refers not only to an alkyl group not having a substituent (unsubstituted alkyl group) but also an alkyl group having a substituent (substituted alkyl group).

In the present specification, in a case where the term "substituent" is simply referred to, examples of substituents include the following substituent T's.

(Substituent T)

Examples of substituent T's include a halogen atom, an alkyl group, a cycloalkyl group, an alkenyl group, a cycloalkenyl group, an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an amino group (including an alkylamino group and an anilino group), an acylamino group, an aminocarbonylamino group, an alkoxycarbonylamino group, an aryloxycarbonylamino group, a sulfamoylamino group, an alkyl or arylsulfonylamino group, a mercapto group, an alkylthio group, an arylthio group, a heterocyclic thio group, a sulfamoyl group, a sulfo group, an alkyl or arylsulfinyl group, an alkyl or aryl sulfonyl group, an acyl group, an aryloxycarbonyl group, an alkyloxycarbonyl group, a carbamoyl group, an aryl or heterocyclic azo group, an imide group, a phosphino group, a phosphinyl group, a phosphinyloxy group, a phosphinylamino group, a silyl group, and the like.

Among the above-mentioned substituents, in substituents having a hydrogen atom, a hydrogen atom portion in the substituent may further be substituted by any of the above-mentioned substituents.

A compound of the embodiment of the present invention is a compound by which high refractive index anisotropy Δn and inhibition of colorability can be compatible. The reason why such effects are obtained is not necessarily clear, but it is thought that refractive index anisotropy Δn is improved by linking a tolan skeleton with a specific linking group while not lengthening an absorption wavelength of the compound.

[Compound]

Hereinafter, the compound of the embodiment of the present invention will be described in detail. The compound of the embodiment of the present invention is represented by General Formula (1).

The compound of the embodiment of the present invention preferably exhibits liquid crystallinity. For the compound to exhibit liquid crystallinity, it is intended that the compound has properties of expressing a mesophase between a crystalline phase (low temperature side) and an isotropic phase (high temperature side) in a case where a temperature is changed. As a specific observation method, optical anisotropy and fluidity derived from a liquid crystalline phase can be confirmed by making an observation under a polarizing microscope while heating or lowering a temperature of the compound with a hot stage system FP90, manufactured by Mettler-Toledo International Inc., or the like.

The compound of the embodiment of the present invention preferably exhibits liquid crystallinity by itself, but it may exhibit liquid crystallinity in a mixed system with other compounds.

As preferable specific examples of the polymerizable group, groups represented by General Formulae (P-1) to (P-19) are mentioned. In the following formulae, * represents a bonding position.

(P-1)

(P-2)

(P-3)

(P-4)

(P-5)

(P-6)

(P-7)

(P-8)

(P-9)

General Formula (I)

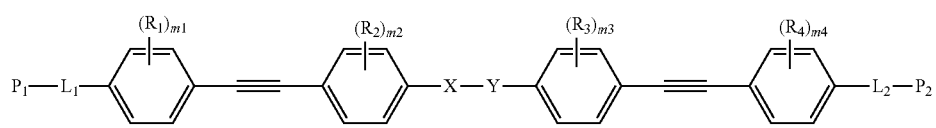

in General Formula (1), $P_1$ and $P_2$ each independently represent a polymerizable group.

The type of the polymerizable group is not particularly limited, and a known polymerizable group is mentioned. From the viewpoint of reactivity, a functional group that can be subjected to addition polymerization reaction is preferable, and a polymerizable ethylenically unsaturated group or a cyclic polymerizable group is more preferable. As the polymerizable group, for example, a (meth)acryloyloxy group, a vinyl group, a maleimide group, an acetyl group, a styryl group, an allyl group, an epoxy group, an oxetane group, and a group containing these groups are mentioned. A hydrogen atom in each of the above groups may be substituted with another substituent such as a halogen atom.

-continued

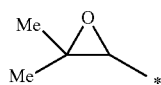

(P-10)

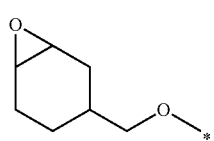

(P-11)

-continued

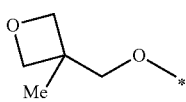
(P-12)

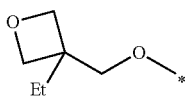
(P-13)

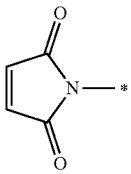
(P-14)

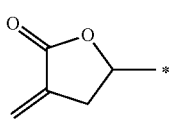
(P-15)

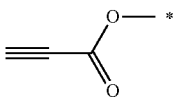
(P-16)

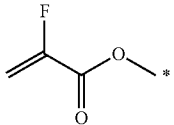
(P-17)

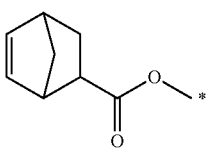
(P-18)

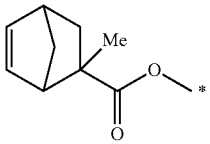
(P-19)

$L_1$ and $L_2$ each independently represent a single bond or a divalent linking group.

Examples of divalent linking groups include an ether group (—O—), a carbonyl group (—CO—), an ester group (—COO—), a thioether group (—S—), —SO$_2$—, —NR— (where R represents a hydrogen atom or an alkyl group), a divalent hydrocarbon group (for example, a saturated hydrocarbon group such as an alkylene group, an alkenylene group (for example, —CH═CH—), an alkynylene group (for example, —C≡C—), and an arylene group), and groups in which these groups are combined.

Among the above-mentioned divalent linking groups, a atom directly bonded to a benzene ring group in General Formula (1) is preferably a carbon atom, and the carbon atom is preferably an sp3 carbon atom (a carbon atom having only a single bond).

As the divalent linking group, a divalent hydrocarbon group which has 1 to 20 carbon atoms and may have a substituent is preferable. One or more methylene groups in the divalent hydrocarbon group each independently may be substituted by —O— or —C(═O)—. One methylene group may be substituted by —O—, and a methylene group adjacent thereto may be substituted by —C(═O)— to form an ester group.

As the substituent that the divalent hydrocarbon group may have, for example, a fluorine atom is preferable.

The divalent hydrocarbon group has 1 to 20 carbon atoms, preferably has 1 to 10 carbon atoms, and more preferably has 1 to 5 carbon atoms.

The divalent hydrocarbon group may be linear or branched, and may have a cyclic structure.

Among the examples, $L_1$ preferably represents a group represented by Formula (A), and $L_2$ preferably represents a group represented by Formula (B).

$$*—Z_1-Sp_1-** \quad \text{Formula (A)}$$

$$*—Z_2-Sp_2-** \quad \text{Formula (B)}$$

Where $Z_1$ and $Z_2$ each independently represent —C($R_{za}$)($R_{zb}$)—.

$R_{za}$ and $R_{zb}$ each independently represent a hydrogen atom or a substituent, where a hydrogen atom is preferable.

$Sp_1$ and $Sp_2$ each independently represent a divalent hydrocarbon group which has 1 to 19 carbon atoms and may have a fluorine atom, or a single bond. One or more methylene groups in the divalent hydrocarbon group each independently may be substituted by —O— or —C(═O)—. One methylene group may be substituted by —O—, and a methylene group adjacent thereto may be substituted by —C(═O)— to form an ester group.

The divalent hydrocarbon group may be linear or branched, and may have a cyclic structure.

*'s respectively represent a bonding position with a benzene ring group directly bonded to $L_1$ or $L_2$, and **'s respectively represent a bonding position with $P_1$ or $P_2$.

X represents —C($R_{xa}$)($R_{xb}$)—. $R_{xa}$ and $R_{xb}$ each independently represent a hydrogen atom or a substituent.

$R_{xa}$ and $R_{xb}$ are preferably hydrogen atoms.

Y represents —C($R_{ya}$)($R_{yb}$)—, —O—, —NR$_{yn}$—, or —S—. $R_{ya}$ and $R_{yb}$ each independently represent a hydrogen atom or a substituent. $R_{yn}$ represents a hydrogen atom or an alkyl group having 1 to 6 carbon atoms (may be linear or branched, may have a cyclic structure, and may further have a substituent).

Among them, Y is preferably —C($R_{ya}$)($R_{yb}$)— or —O—, and is more preferably —C($R_{ya}$)($R_{yb}$)— from the viewpoint of further inhibiting coloration of the compound.

$R_1$ to $R_4$ each independently represent a substituent.

The above-mentioned substituents are each independently preferably an alkyl group having 1 to 20 carbon atoms (preferably 1 to 10 carbon atoms and more preferably 2 to 5 carbon atoms), an alkoxy group having 1 to 20 carbon atoms, an alkanoyl group having 1 to 20 carbon atoms, an alkanoyloxy group having 1 to 20 carbon atoms, an alkyloxycarbonyl group having 1 to 20 carbon atoms (preferably 2 to 6 carbon atoms), an alkylamino group having 1 to 20 carbon atoms, an alkylaminocarbonyl group having 1 to 20 carbon atoms, an alkanoylamino group having 1 to 20 carbon atoms, a cyano group, a nitro group, a halogen atom, or a group having a polymerizable group (where examples of polymerizable groups include the groups exemplified in the description of $P_1$ and $P_2$).

In a case where the above-mentioned substituent can be linear or branched, the above-mentioned substituent may be linear or branched. In addition, the substituent may have a cyclic structure in a case where it can have the cyclic structure.

One or more methylene groups in the alkyl group and an alkyl group moiety of the above-mentioned substituent (for example, a moiety other than —O— in the alkoxy group) may be independently substituted by —O— or —C(=O)—, respectively.

Furthermore, the above-mentioned substituents may further have a substituent (preferably a fluorine atom) in a case where the substituent can further have a substituent. For example, it is also preferable that the alkyl group be a fluoroalkyl group (for example, a perfluoroalkyl group having 1 to 10 carbon atoms such as trifluoromethyl group). Furthermore, for example, it is also preferable that an alkyl group moiety of the above-mentioned substituent have a fluorine atom.

Among them, as a substituent, the alkyl group, the alkyloxycarbonyl group, or the alkylaminocarbonyl group is preferable; an alkyl group having 2 or more carbon atoms, a fluoromethyl group (preferably a trifluoromethyl group), the alkyloxycarbonyl group, or the alkylaminocarbonyl group is more preferable; the alkyloxycarbonyl group or the alkylaminocarbonyl group is even more preferable; and the alkyloxycarbonyl group is particularly preferable, from the viewpoint of excellent liquid crystallinity and solubility of the compound.

$m_1$ to $m_4$ each independently represent an integer of 0 to 4. In a case where $R_1$ to $R_4$ respectively matched therewith are each present in plurality because there are two or more of $m_1$ to $m_4$, the $R_1$'s to $R_4$'s each may be the same as or different from each other.

It is preferable that at least one of $m_1$, $m_2$, $m_3$, or $m_4$ represent an integer of 1 or more from the viewpoint of excellent liquid crystallinity and solubility of the compound. Among them, it is preferable that $m_3$ represent an integer of 1 or more.

Among them, it is preferable that at least one of $m_1$, $m_2$, $m_3$, or $m_4$ represent an integer of 1 or more, and at least one of $R_1$, $R_2$, $R_3$, or $R_4$ respectively matched with $m_1$, $m_2$, $m_3$, or $m_4$ each representing an integer of 1 or more be the alkyl group, the alkyloxycarbonyl group, or the alkylaminocarbonyl group. It is more preferable that at least one of $m_1$, $m_2$, $m_3$, or $m_4$ represent an integer of 1 or more, and at least one of $R_1$, $R_2$, $R_3$, or $R_4$ respectively matched with $m_1$, $m_2$, $m_3$, or $m_4$ each representing an integer of 1 or more be an alkyl group having 2 or more carbon atoms, a fluoromethyl group (preferably a trifluoromethyl group), the alkyloxycarbonyl group, or the alkylaminocarbonyl group. It is even more preferable that at least one of $m_1$, $m_2$, $m_3$, or $m_4$ represent an integer of 1 or more, and at least one of $R_1$, $R_2$, $R_3$, or $R_4$ respectively matched with $m_1$, $m_2$, $m_3$, or $m_4$ each representing an integer of 1 or more be the alkyloxycarbonyl group or the alkylaminocarbonyl group. It is particularly preferable that at least one of $m_1$, $m_2$, $m_3$, or $m_4$ represent an integer of 1 or more, and at least one of $R_1$, $R_2$, $R_3$, or $R_4$ respectively matched with $m_1$, $m_2$, $m_3$, or $m_4$ each representing an integer of 1 or more be the alkyloxycarbonyl group. It is particularly preferable that $m_3$ represent an integer of 1 or more, and at least one of $R_3$ be the alkyl group, the alkyloxycarbonyl group, or the alkylaminocarbonyl group.

The sentence "at least one of $R_1$, $R_2$, $R_3$, or $R_4$ respectively matched with $m_1$, $m_2$, $m_3$, or $m_4$ each representing an integer of 1 or more is the alkyl group or the like" refers to, for example, an aspect in which $R_1$ matched with $m_1$ is the group described above in a case where $m_1$ represents an integer of 1 or more and $m_2$ to $m_4$ are 0. Furthermore, as another example, the sentence refers to an aspect in which at least one of $R_1$ matched with $m_1$ or $R_2$ matched with $m_2$ is the group described above in a case where $m_1$ and $m_2$ represent an integer of 1 or more and $m_3$ and $m_4$ are 0.

Refractive index anisotropy Δn of the compound of the embodiment of the present invention is not particularly limited, and it is preferably 0.23 or more, more preferably 0.28 or more, and even more preferably 0.30 or more. An upper limit thereof is not particularly limited, and is 0.60 or less in many cases.

As a method of measuring the Δn, a method using a wedge-shaped liquid crystal cell described on page 202 of the Liquid Crystal Handbook (edited by Liquid Crystal Handbook Editing Committee, published by Maruzen Co., Ltd.) is generally used. In a case of a compound which is liable to crystallize, it is also possible to carry out evaluation with a mixture thereof with other liquid crystals and to estimate Δn from extrapolated values thereof.

The Δn corresponds to a measurement value at a wavelength of 550 nm at 30° C.

The compound of the embodiment of the present invention can be synthesized by a known method.

Examples of the compound of the embodiment of the present invention include the following compounds.

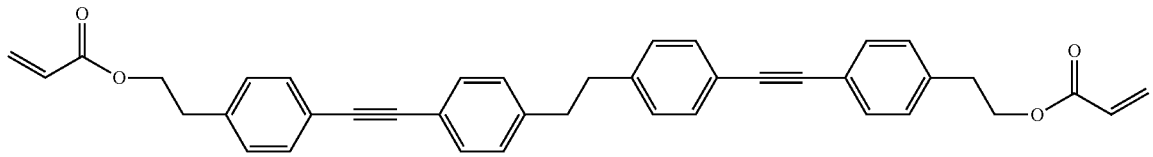

A-1

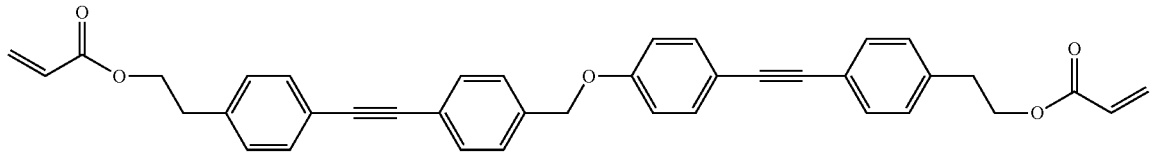

A-2

A-3
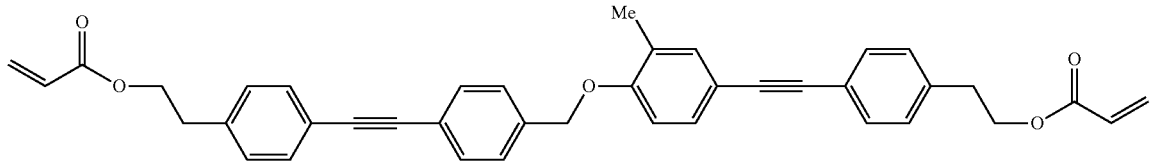
A-4
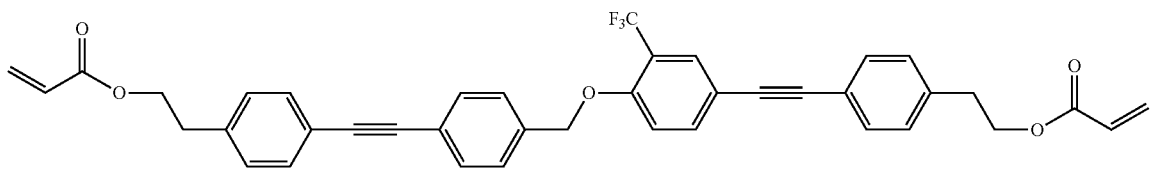
A-5
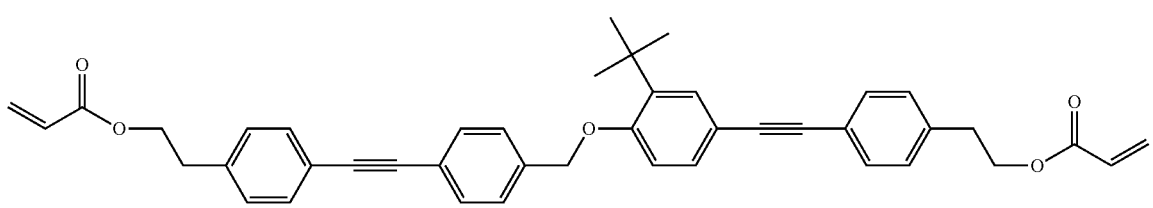
A-6
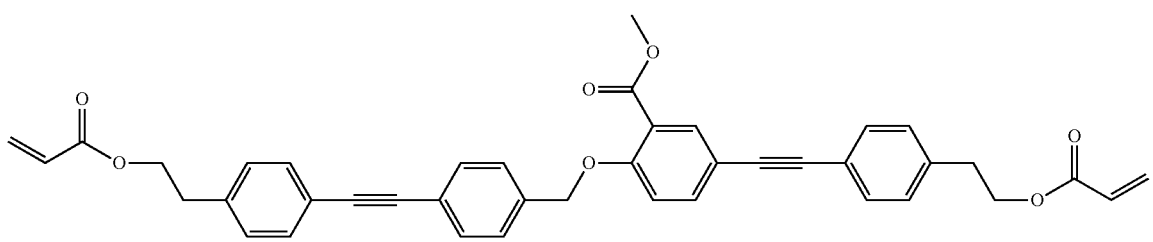
A-7
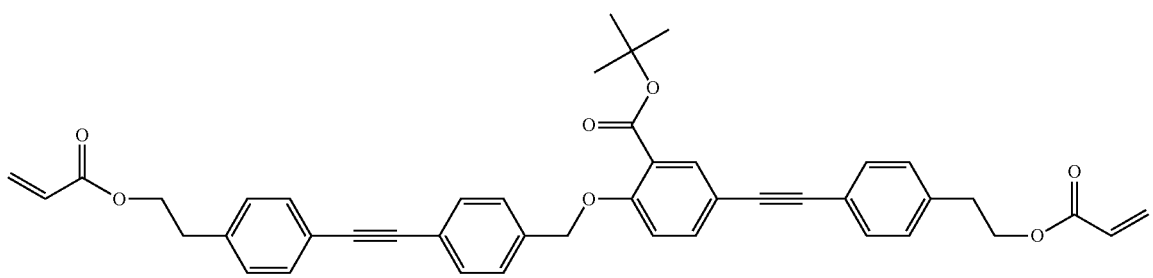
A-8
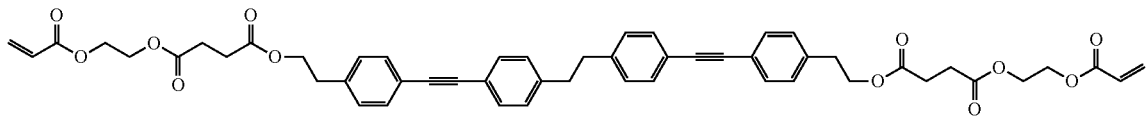
A-9
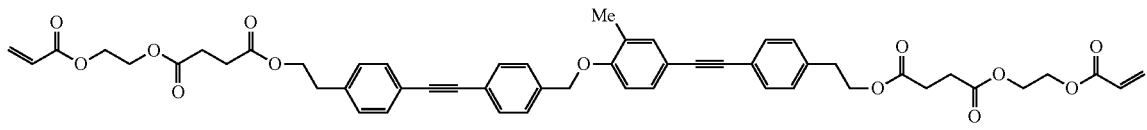

A-10
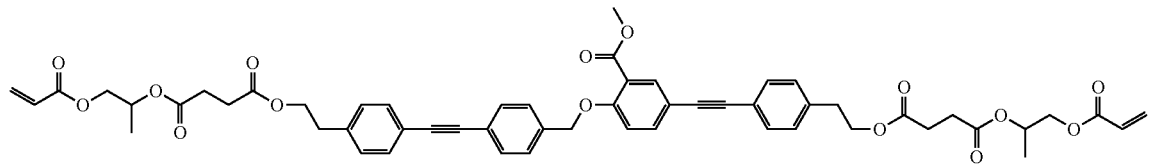
A-11
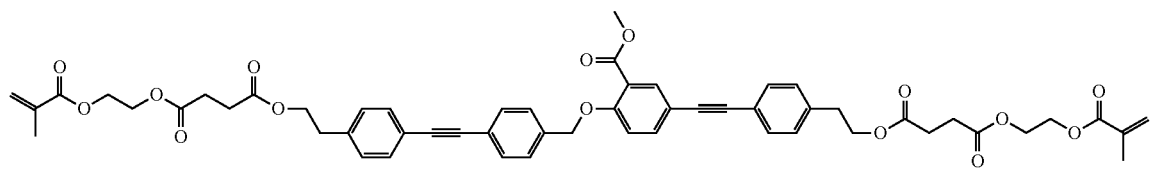
A-12
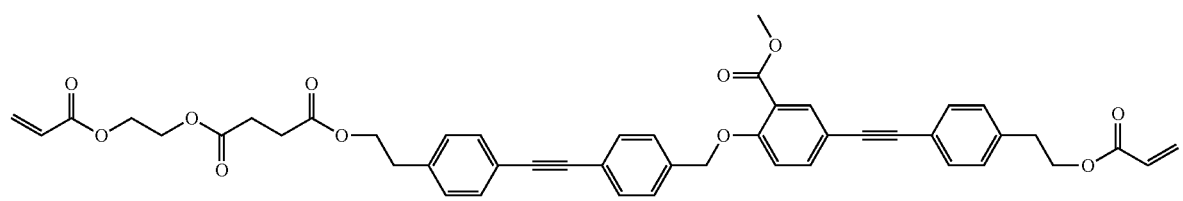
A-13
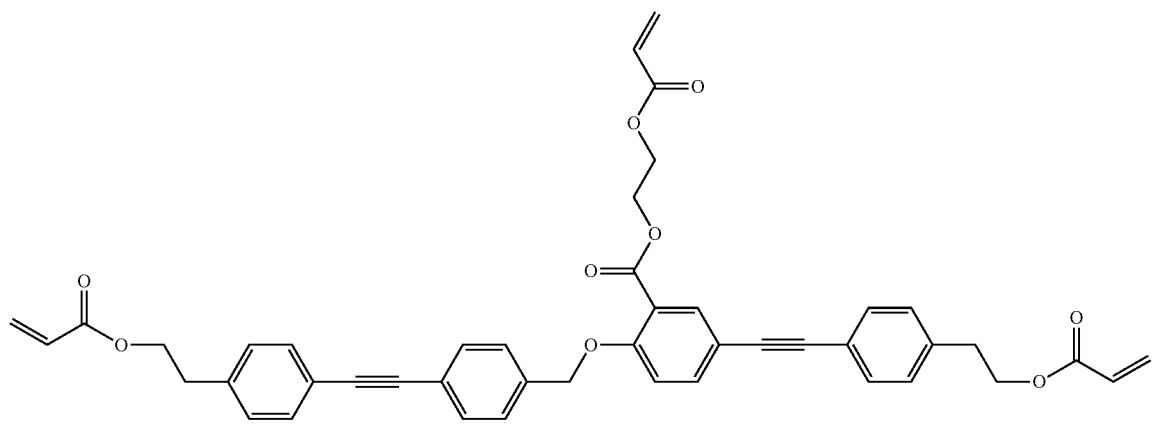
A-14
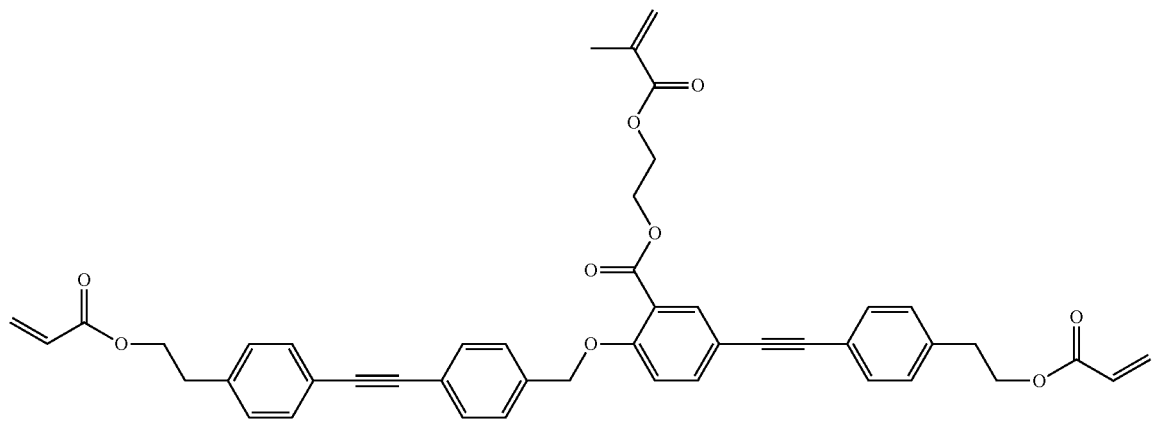

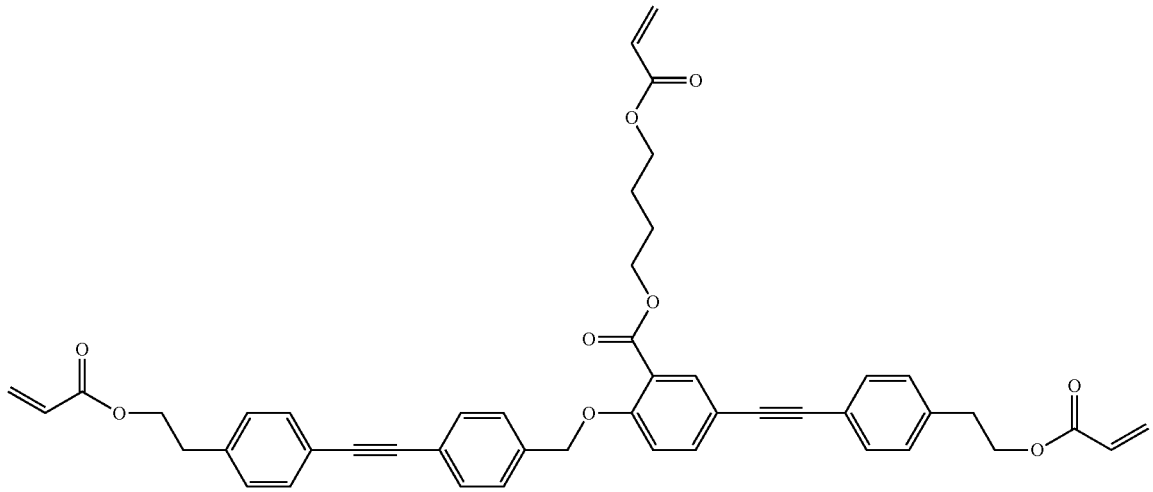

[Composition]

The compound of the embodiment of the present invention can be used in a form of a composition containing the compound. The composition may contain components other than the compound of the embodiment of the present invention.

A content of the compound of the embodiment of the present invention in the composition is not particularly limited, and it is preferably 20% to 100% by mass, and more preferably 40% to 100% by mass with respect to a total mass of solid contents in the composition.

The solid contents mean components (non-volatile contents) other than a solvent in the composition. In a case of components other than a solvent, they are regarded as solid contents even in a case where they are components having the properties of liquids.

In the composition, the compound of the embodiment of the present invention may be used alone or in combination of two or more kinds thereof. In a case where two or more kinds are used, a total content thereof is preferably within the above-mentioned range.

Hereinafter, other components contained in the composition will be described in detail.

<Other Liquid Crystal Compounds>

The composition may contain other liquid crystal compounds other than the compound of the embodiment of the present invention.

The other liquid crystal compound may be a rod-shaped liquid crystal compound or a disc-shaped liquid crystal compound, but a rod-shaped liquid crystal compound is preferable. In addition, the other liquid crystal compound is preferably a liquid crystal compound having a polymerizable group (other polymerizable liquid crystal compound).

Examples of rod-shaped liquid crystal compounds which are other liquid crystal compounds include a rod-shaped nematic liquid crystal compound. Preferable examples of rod-shaped nematic liquid crystal compounds include azomethines, azoxys, cyanobiphenyls, cyanophenyl esters, benzoic acid esters, cyclohexanecarboxylic acid phenyl esters, cyanophenylcyclohexanes, cyano-substituted phenylpyrimidines, alkoxy-substituted phenylpyrimidines, phenyldioxanes, tolans, and alkenylcyclohexylbenzonitriles. High-molecular liquid crystal compounds can also be used as well as low-molecular liquid crystal compounds.

The liquid crystal compound having a polymerizable group can be obtained by introducing the polymerizable group into the liquid crystal compound. Examples of polymerizable groups include the polymerizable groups exemplified for $P_1$ and $P_2$ of General Formula (1).

The number of polymerizable groups contained in the liquid crystal compound having a polymerizable group is preferably 1 to 6, and is more preferably 1 to 3.

The other liquid crystal compounds preferably have high Δn. Specifically, 0.15 or more is preferable, 0.18 or more is more preferable, and 0.22 or more is even more preferable. An upper limit thereof is not particularly limited, and is 0.60 or less in many cases.

In addition, by mixing the compound of the embodiment of the present invention with the other liquid crystal compounds and using the mixture, a crystallization temperature as a whole can be significantly lowered.

Examples of other liquid crystal compounds include compounds disclosed in Makromol. Chem., Vol. 190, page 2255 (1989), Advanced Materials, Vol. 5, page 107 (1993), U.S. Pat. Nos. 4,683,327A, 4,983,479A, 5,622,648A, 5,770,107A, WO95/022586A, WO95/024455A, WO97/000600A, WO98/023580A, WO98/052905A, JP1989-272551A (JP-H01-272551A), JP1994-016616A (JP-H06-016616A), JP1995-110469A (JP-H07-110469A), JP1999-080081A (JP-H11-080081A), JP2001-328973A, and the like.

In a case where the composition contains the other liquid crystal compounds, a content of the other liquid crystal compounds in the composition is not particularly limited, but it is preferably 10% to 200% by mass, and is more preferably 50% to 150% by mass with respect to a total mass of the compound of the embodiment of the present invention.

In the composition, the other liquid crystal compound may be used alone or in combination of two or more kinds thereof. In a case where two or more kinds are used, a total content thereof is preferably within the above-mentioned range.

(Polymerization Initiator)

The composition may contain a polymerization initiator.

The polymerization initiator is preferably a photopolymerization initiator which is capable of initiating a polymerization reaction by ultraviolet irradiation. As the photopolymerization initiator, for example, an α-carbonyl compound, acyloin ether, an α-hydrocarbon-substituted aromatic acyloin compound, a polynuclear quinone compound, a phenazine compound, and an oxadiazole compound are mentioned. In addition, a compound having an oxime ester structure is also preferable.

In a case where the composition contains the polymerization initiator, a content of the polymerization initiator in the composition is not particularly limited, but it is preferably 0.1% to 20% by mass, and is more preferably 1% to 8% by mass with respect to a total mass of the compound of the embodiment of the present invention (with respect to a total mass of the compound of the embodiment of the present invention and other polymerizable liquid crystal compounds in a case where the composition contains the other polymerizable liquid crystal compounds).

In the composition, the polymerization initiator may be used alone or in combination of two or more kinds thereof. In a case where two or more kinds are used, a total content thereof is preferably within the above-mentioned range.

<Surfactant>

The composition may contain a surfactant that contributes to the formation of a stable or rapid liquid crystalline phase (for example, a nematic phase, a cholesteric phase).

Examples of surfactants include a fluorine-containing (meth)acrylate polymer, compounds represented by General Formulae (X1) to (X3) disclosed in WO2011/162291A, compounds represented by General Formula (I) disclosed in paragraphs 0082 to 0090 of J2014-119605A, and compounds disclosed in paragraphs 0020 to 0031 of JP2013-047204A. These compounds can reduce a tilt angle of molecules of a liquid crystal compound or can cause a liquid crystal compound to be substantially horizontally aligned at an air interface of a layer.

In the present specification, the term "horizontal alignment" means that a molecular axis of the liquid crystal compound (which corresponds to a long axis of the liquid crystal compound in a case where the liquid crystal compound is a rod-shaped liquid crystal compound) is parallel to a film surface, but the axis is not required to be strictly parallel, and in the present specification, the term means an alignment in which a tilt angle with the film surface is less than 20 degrees. In a case where the liquid crystal compound is horizontally aligned near the air interface, alignment defects are less likely to occur, and therefore transparency in a visible light region is increased. On the other hand, in a case where molecules of the liquid crystal compound are aligned at a large tilt angle, for example, in a case where a cholesteric phase is formed, a helical axis is deviated from the normal to the film surface. These cases are not preferable because, accordingly, reflectance is lowered, or fingerprint patterns are generated and thereby haze may be increased or diffractive.

Examples of fluorine-containing (meth) acrylate-based polymers that can be used as the surfactant also include polymers disclosed in paragraphs 0018 to 0043 of JP2007-272185A.

In a case where the composition contains the surfactant, a content of the surfactant is not particularly limited, but it is preferably 0.001% to 10% by mass, and is more preferably 0.05% to 3% by mass with respect to a total mass of the compound of the embodiment of the present invention (with respect to a total mass of the compound of the embodiment of the present invention and other liquid crystal compounds in a case where the composition contains the other liquid crystal compounds).

In the composition, the surfactant may be used alone or in combination of two or more kinds thereof. In a case where two or more kinds are used, a total content thereof is preferably within the above-mentioned range.

<Chiral Agent>

The composition may contain a chiral agent. In a case where the composition contains the chiral agent, a cholesteric phase can be formed.

A type of the chiral agent is not particularly limited. The chiral agent may be liquid crystalline or non-liquid crystalline. The chiral agent generally contains an asymmetric carbon atom. However, an axial asymmetric compound or a planar asymmetric compound which does not contain any asymmetric carbon atom can also be used as the chiral agent. As the axial asymmetric compound or the planar asymmetric compound, binaphthyl, helicene, paracyclophane, and derivatives thereof are mentioned. The chiral agent may have a polymerizable group.

In a case where the composition contains the chiral agent, a content of the chiral agent in the composition is not particularly limited, but it is preferably 0.1% to 15% by mass, and is more preferably 1.0% to 10% by mass with respect to a total mass of the compound of the embodiment of the present invention (with respect to a total mass of the compound of the embodiment of the present invention and other liquid crystal compounds in a case where the composition contains the other liquid crystal compounds).

In the composition, the chiral agent may be used alone or in combination of two or more kinds thereof. In a case where two or more kinds are used, a total content thereof is preferably within the above-mentioned range.

<Solvent>

The composition may contain a solvent. The solvent is preferably capable of dissolving each component of the composition, and examples thereof include chloroform. In a case where the composition contains the solvent, a content of the solvent in the composition is preferably such that a concentration of solid contents of the composition is 0.5% to 20% by mass, and a content of the solvent in the composition is more preferably such that a concentration of solid contents of the composition is 1 to 10.

In the composition, the solvent may be used alone or in combination of two or more kinds thereof. In a case where two or more kinds are used, a total content thereof is preferably within the above-mentioned range.

Besides the above, the composition may also contain other additives such as an antioxidant, an ultraviolet absorber, a sensitizer, a stabilizer, a plasticizer, a chain transfer agent, a polymerization inhibitor, an anti-foaming agent, a leveling agent, a thickener, a flame retardant, a surfactant, a dispersant, and a coloring material such as a dye and a pigment.

[Cured Object]

The present invention also includes a cured object obtained by curing the above-described composition.

<Curing Method and Cured Object>

A method of curing (polymerizing and curing) the above composition is not particularly limited, and a known method can be adopted. For example, a form having a step X in which a predetermined substrate and the composition are brought into contact with each other to form a composition layer on the substrate, and a step Y in which the composition layer is subjected to a heat treatment so that the compound of the embodiment of the present invention is aligned, and then is subjected to a curing treatment. According to the present form, the compound of the embodiment of the present invention can be immobilized in an aligned state, and a layer in which a so-called optically anisotropic body or a cholesteric liquid crystalline phase is fixed can be formed.

Hereinafter, procedures for the step X and the step Y will be described in detail.

The step X is a step of bringing a predetermined substrate into contact with the composition to form a composition layer on the substrate. A type of the substrate to be used is not particularly limited, and known substrates (for example, a resin substrate, a glass substrate, a ceramic substrate, a semiconductor substrate, and a metal substrate) are mentioned.

A method of bringing the substrate into contact with the composition is not particularly limited, and examples thereof include a method of coating the composition on the substrate and a method of immersing the substrate in the composition.

After bringing the substrate into contact with the composition, if necessary, a drying treatment may be carried out in order to remove a solvent from the composition layer on the substrate.

The step Y is a step of subjecting the composition layer to a heat treatment so that the compound of the embodiment of the present invention is aligned, and then subjecting the same to a curing treatment.

By subjecting the composition layer to a heat treatment, the compound of the embodiment of the present invention is aligned and a liquid crystalline phase is formed. For example, in a case where a chiral agent is contained in the composition layer, a cholesteric liquid crystalline phase is formed.

A condition for the heat treatment is not particularly limited, and an optimal condition is selected depending on a type of the compound of the embodiment of the present invention.

A method for the curing treatment is not particularly limited, and a photo-curing treatment and a thermal-curing treatment are mentioned. Among these, a light irradiation treatment is preferable, and an ultraviolet irradiation treatment is more preferable.

For the ultraviolet irradiation, a light source such as an ultraviolet lamp is used.

The cured object obtained by the above treatment corresponds to a layer in which a liquid crystalline phase is fixed. In particular, in a case where the composition contains a chiral agent, a layer is formed in which a cholesteric liquid crystalline phase is fixed.

These layers do not need to exhibit liquid crystallinity anymore. More specifically, for example, as a state in which the cholesteric liquid crystalline phase is "fixed," the most typical and preferable form is a state in which alignment of the compound of the embodiment of the present invention which is a cholesteric liquid crystalline phase is retained. More specifically, the state is preferably a state in which within a temperature range of usually 0° C. to 50° C., and, under more severe conditions, −30° C. to 70° C., no fluidity is exhibited in the layer, no changes in alignment form occur due to an external field or an external force, and a fixed alignment form can be kept in a stable and continuous manner.

[Optically Anisotropic Body and Reflective Film]

A cured object is obtained by subjecting the composition to a curing treatment as described above.

The cured object obtained by curing the composition of the embodiment of the present invention can be applied to various uses, and, for example, an optically anisotropic body and a reflective film are mentioned. In other words, an optically anisotropic body or a reflective film obtained by curing the above composition is mentioned as a suitable form.

The optically anisotropic body is intended to have a substance having optical anisotropy.

In addition, the reflective film corresponds to a layer in which the above-described cholesteric liquid crystalline phase is fixed, and can reflect light in a predetermined reflection band.

EXAMPLES

Hereinafter, the present invention will be described more specifically with reference to examples. Materials, reagents, proportions, operations, and the like shown in the following examples can be appropriately changed without departing from the gist of the present invention. Accordingly, the scope of the present invention is not limited to specific examples shown below.

[Synthesis of Compound]

Synthesis Example 1: Synthesis of Compound A-1

A compound A-1 was synthesized according to the following scheme.

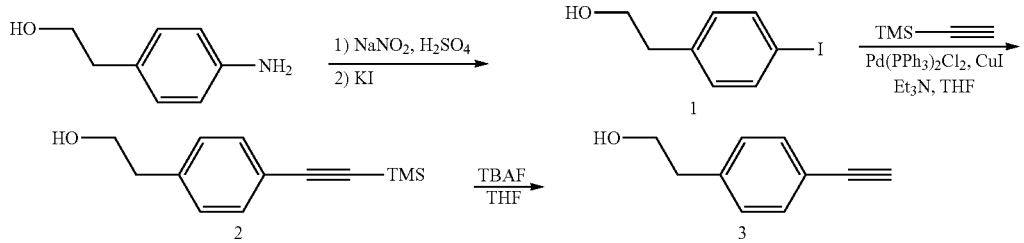

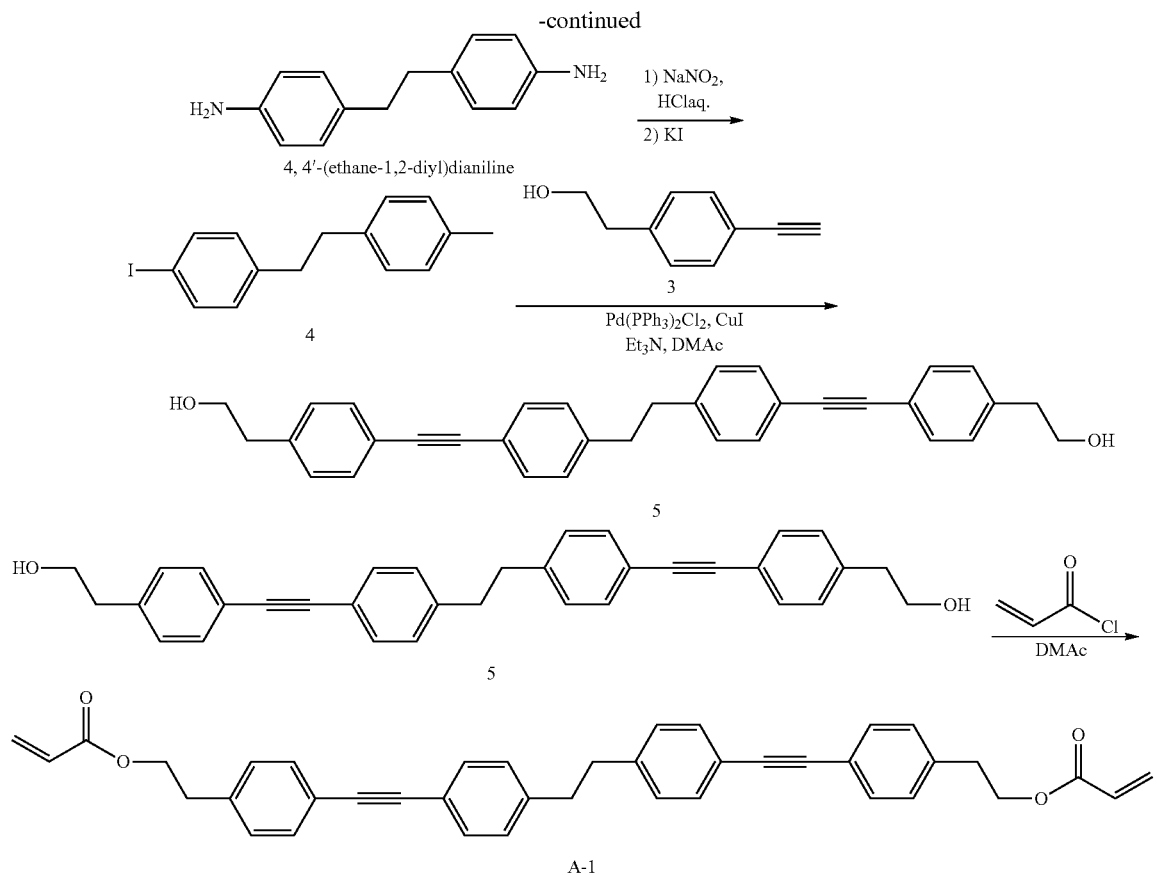

(1) Synthesis of Compound 1

4-Aminophenyl-2-ethanol (132.1 g, 0.96 mol) was dissolved in water (1056 mL) and concentrated sulfuric acid 90 mL (1.69 mol). An aqueous solution in which sodium nitrite (83.0 g, 1.20 mol) was dissolved in water (264 mL) was added dropwise to this solution while maintaining the temperature at 5° C. or lower to carry out diazotization. Thereafter, an aqueous solution in which potassium iodide (545.1 g, 3.28 mol) was dissolved in water (660 mL) was added dropwise to this solution, and the mixture was stirred at room temperature for 2 hours. After the obtained solution was extracted twice with ethyl acetate, the obtained organic phases were combined, washed with an aqueous solution of 10% by mass sodium thiosulfate and saturated saline, and dried with magnesium sulfate. After filtering the dried organic phase, the solvent was distilled off under reduced pressure, the obtained residue was purified by flash column chromatography, and thereby a pale yellow oily compound 1 (195.4 g, 0.79 mol) was obtained. The yield was 81.8%.

(2) Synthesis of Compound 2

Under a nitrogen atmosphere, the compound 1 (195.4 g, 0.79 mol) and trimethylsilyl acetylene (116.0 g, 1.18 mol) were dissolved in a mixed solution of tetrahydrofuran (1974 mL) and triethylamine (796.9 g, 7.88 mol). After nitrogen bubbling of the obtained solution for 30 minutes, Pd(PPh$_3$)$_2$Cl$_2$ (27.6 g, 39.4 mmol) and CuI (15.0 mg, 78.8 mmol) were added to the solution, and the solution was stirred at 55° C. for 2 hours. After cooling the solution to room temperature, insoluble materials were removed from the solution by filtration. The obtained solution was washed once with a saturated aqueous solution of ammonium chloride and once with water and saturated saline, and dried over magnesium sulfate. After filtering the dried organic phase, the solvent was distilled off under reduced pressure, the obtained residue was purified by flash column chromatography, and thereby a pale yellow oily compound 2 (163.4 g, 0.75 mol) was obtained. The yield was 94.7%.

(3) Synthesis of Compound 3

The compound 2 (163.4 g, 0.75 mmol) was dissolved in tetrahydrofuran (820 ml). A 1 M solution of tetrabutylammonium fluoride in tetrahydrofuran (822.9 ml, 0.82 mol) was added to the obtained solution, and the solution was stirred at room temperature for 1 hour. To the obtained solution was added 1 N hydrochloric acid, and then extracted with ethyl acetate four times. The organic phase obtained by the extraction was washed once with saline and dried over magnesium sulfate. After filtering the dried organic phase, the solvent was distilled off under reduced pressure, the obtained residue was purified by flash column chromatography, and thereby a pale yellow oily compound 3 (103.7 g, 0.71 mol) was obtained. The yield was 94.6%.

(4) Synthesis of Compound 4

4,4'-Ethylenedianiline (2.00 g, 9.42 mmol) was dissolved in 1N aqueous hydrochloric acid (in 113 mL). An aqueous solution in which sodium nitrite (1.95 g, 28.3 mmol) was dissolved in water (10 mL) was added dropwise to this solution while maintaining the temperature at 5° C. or lower to carry out diazotization. Thereafter, an aqueous solution in which potassium iodide (4.24 g, 28.3 mmol) was dissolved in water (10 mL) was added dropwise to the solution, and the mixture was stirred at room temperature for 2 hours. The precipitated solid was filtered once, washed with water, and thereafter, redissolved in ethyl acetate, washed with saturated saline, and dried over magnesium sulfate. After filtering the dried organic phase, the solvent was distilled off under reduced pressure, the obtained residue was purified by flash column chromatography, and thereby a compound 4 (0.45 g, 1.04 mmol) was obtained. The yield was 11.0%.

(5) Synthesis of Compound 5

Under a nitrogen atmosphere, the compound 4 (0.40 g, 0.92 mmol) and the compound 3 (0.30 g, 2.05 mmol) were dissolved in a mixed solution of dimethylacetamide (10 mL) and triethylamine (0.93 g, 9.18 mmol). After nitrogen bubbling of the obtained solution for 30 minutes, $Pd(PPh_3)_2Cl_2$ (32.3 mg, 0.046 mmol) and CuI (17.5 mg, 0.092 mmol) were added to the solution, and the solution was stirred at 55° C. for 2 hours. After cooling the solution to room temperature, insoluble materials were removed from the solution by filtration. The precipitated solid obtained by adding water to the obtained solution was filtered. Thereafter, it was suspended and washed in methanol, and thereby a compound 5 (0.25 g, 0.53 mmol) was obtained. The yield was 57.7%.

(6) Synthesis of Compound A-1

The compound 5 (0.25 g, 0.53 mmol) was dissolved in dimethylacetamide (10 ml). Acrylic chloride (0.37 ml, 4.6 mmol) and triethylamine (0.64 mL, 4.6 mmol) were added under ice cooling, and the solution was stirred at room temperature for 2 hours. To the obtained solution was added 1 N hydrochloric acid, and then extracted with ethyl acetate. The organic phase obtained by the extraction was washed once with a saturated aqueous solution of sodium hydrogen carbonate and saturated saline, and dried over magnesium sulfate. After filtering the dried organic phase, the solvent was distilled off under reduced pressure, the obtained residue was purified by flash column chromatography, and thereby a compound A-1 (0.18 g, 0.31 mmol) was obtained. The yield was 58.7%.

The results of identifying the obtained compound A-1 using $^1$H-NMR (Nuclear Magnetic Resonance) were as follows.

$^1$H-NMR (CDCl$_3$): δ=2.82 (t,4H), 3.00 (t,4H), 4.37 (t,4H), 5.82 (d,2H), 6.10 (dd,2H), 6.38 (d,2H), 7.10 (d,4H), 7.20 (d,4H), 7.45 (m,8H)

Synthesis Example 2: Synthesis of Compound A-2

A compound A-2 was synthesized according to the following scheme.

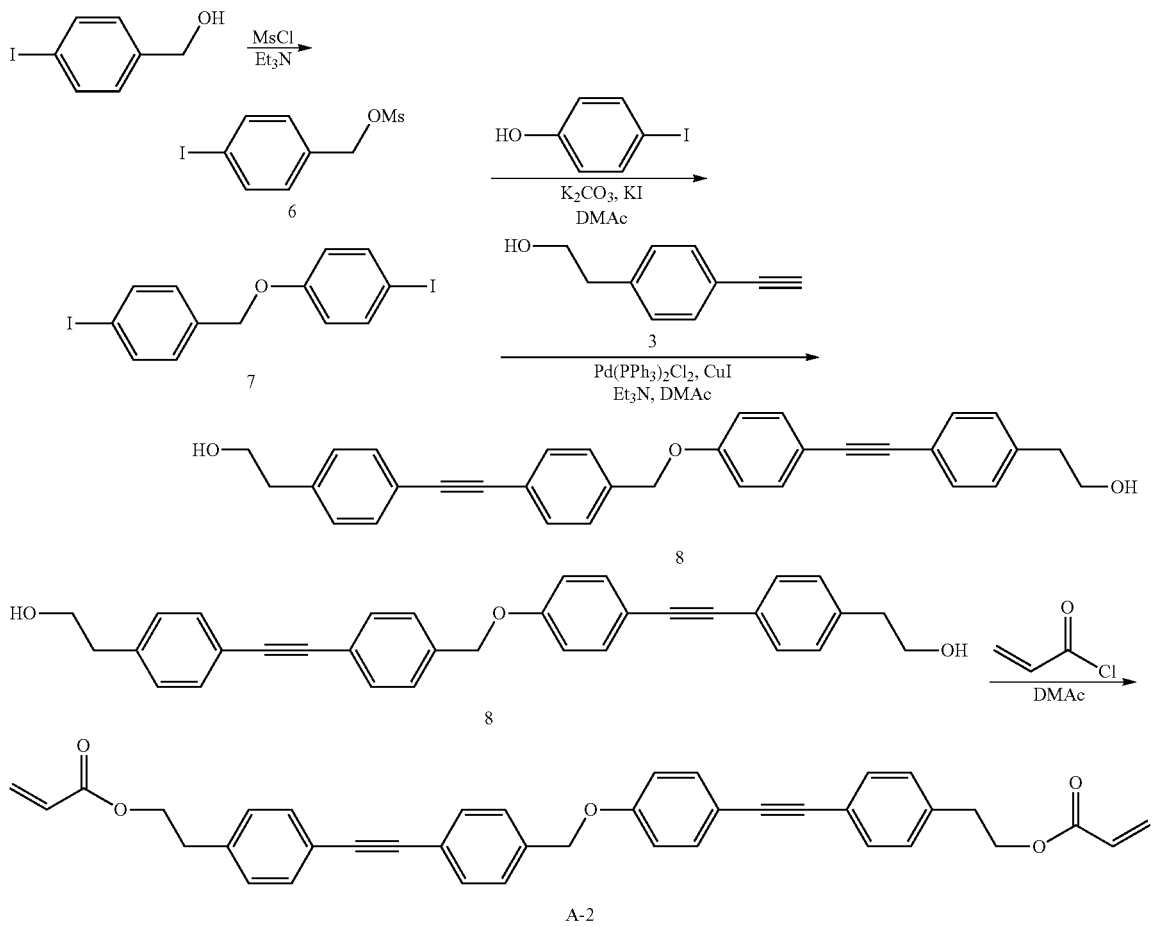

(7) Synthesis of Compound 6

4-Iodobenzyl alcohol (30.0 g, 0.128 mol) was dissolved in tetrahydrofuran (150 mL) to obtain a solution. Methanesulfonyl chloride (15.4 g, 0.135 mol) and triethylamine (14.3 g, 0.141 mol) were added to the obtained solution under ice cooling, and the mixture was stirred at room temperature for 3 hours. Ethyl acetate and water were added to the obtained solution for extraction. Thereafter, the organic phase was washed with water and saturated saline, and dried over magnesium sulfate. After filtering the dried organic phase, the solvent was distilled off under reduced pressure, hexane was added to the obtained residue for suspension washing, and thereby a compound 6 (38.4 g, 0.123 mol) was obtained. The yield was 96.1%.

(8) Synthesis of Compound 7

The compound 6 (5.00 g, 16.0 mmol) and 4-iodophenol (3.52 g, 16.0 mmol) were dissolved in dimethylacetamide (30 mL) to obtain a solution. Potassium carbonate (2.65 g, 19.2 mmol) and potassium iodide (0.27 g, 1.63 mmol) were added to the solution, and the mixture was stirred at 85° C. for 2 hours. The solution was cooled to room temperature, and then extracted by adding ethyl acetate and water. Thereafter, the organic phase was washed with 1N aqueous hydrochloric acid, a saturated aqueous solution of sodium hydrogen carbonate, and saturated saline, and dried over magnesium sulfate. After filtering the dried organic phase, the solvent was distilled off under reduced pressure, methanol was added to the obtained residue for suspension washing, and thereby a compound 7 (4.84 g, 11.1 mmol). The yield was 69.4%.

(9) Synthesis of Compound 8

A compound 8 was synthesized in the same manner as in (5) except that the compound 7 was used instead of the compound 4 in the synthesis (5) of the compound 5.

(10) Synthesis of Compound A-2

A compound A-2 was synthesized in the same manner as in (6) except that the compound 8 was used instead of the compound 5 in Synthesis (6) of the compound A-1.

The results of identifying the obtained compound A-2 using $^1$H-NMR (Nuclear Magnetic Resonance) were as follows.

$^1$H-NMR (CDCl$_3$): δ=2.99 (t,4H), 4.38 (t,4H), 5.10 (s,2H), 5.81 (d,2H), 6.10 (dd,2H), 6.38 (d,2H), 6.92 (d,2H), 7.20 (m,4H), 7.44 (m,8H), 7.55 (d,2H)

Synthesis Example 3: Synthesis of Compound A-3

A compound A-3 was synthesized in the same manner except that 2-methyl-4-iodophenol was used instead of 4-iodophenol in the synthesis of the compound A-2.

The results of identifying the obtained compound A-3 using $^1$H-NMR were as follows.

$^1$H-NMR (CDCl$_3$): δ=2.29 (s,3H), 2.99 (t,4H), 4.38 (t,4H), 5.10 (s,2H), 5.81 (d,2H), 6.10 (dd,2H), 6.38 (d,2H), 6.83 (d,1H), 7.20 (m,4H), 7.32 (d,2H), 7.44 (m,6H), 7.55 (d,2H)

Synthesis Example 4: Synthesis of Compound A-4

A compound A-4 was synthesized in the same manner except that 2-trifluoromethyl-4-bromophenol was used instead of 4-iodophenol in the synthesis of the compound A-2.

The results of identifying the obtained compound A-4 using $^1$H-NMR were as follows.

$^1$H-NMR (CDCl$_3$): δ=2.99 (t,4H), 4.38 (t,4H), 5.23 (s,2H), 5.81 (d,2H), 6.10 (dd,2H), 6.38 (d,2H), 6.98 (d,1H), 7.21 (m,4H), 7.44 (m,6H), 7.52 (d,2H), 7.60 (d,1H), 7.75 (s,1H)

Synthesis Example 5: Synthesis of Compound A-5

A compound A-5 was synthesized in the same manner except that 2-tert-butyl-4-bromophenol synthesized by the following method was used instead of 4-iodophenol in the synthesis of the compound A-2.

(11) Synthesis of 2-tert-butyl-4-bromophenol

2-Tert-butylphenol (10.0 g, 66.6 mmol) was dissolved in chloroform (100 mL) to obtain a solution. Tetrabutylammonium tribromide (38.6 g, 80.0 mmol) was added to the solution. The solution was stirred at room temperature for 1 hour, 1N aqueous hydrochloric acid was added thereto, and the mixture was extracted with chloroform. The obtained organic phase was further washed with 1N aqueous hydrochloric acid, a 10% saline, and saturated saline, and dried over magnesium sulfate. After filtering the dried organic phase, the solvent was distilled off under reduced pressure, the obtained residue was purified by flash column chromatography, and thereby 2-tert-butyl-4-bromophenol (6.60 g, 28.8 mmol) was obtained. The yield was 43.3%.

The results of identifying the obtained compound A-5 using $^1$H-NMR were as follows.

$^1$H-NMR (CDCl$_3$): δ=1.40 (s,9H), 3.00 (t,4H), 4.38 (t,4H), 5.13 (s,2H), 5.81 (d,2H), 6.10 (dd,2H), 6.38 (d,2H), 6.88 (d,1H), 7.21 (m,4H), 7.35 (d,1H), 7.45 (m,7H), 7.56 (d,2H)

Synthesis Example 6: Synthesis of Compound A-6

A compound A-6 was synthesized in the same manner except that 2-methoxycarbonyl-4-iodophenol was used instead of 4-iodophenol in the synthesis of the compound A-2.

The results of identifying the obtained compound A-6 using $^1$H-NMR were as follows.

$^1$H-NMR (CDCl$_3$): δ=2.99 (t,4H), 3.89 (s,3H), 4.38 (t,4H), 5.21 (s,2H), 5.81 (d,2H), 6.10 (dd,2H), 6.38 (d,2H), 6.98 (d,1H), 7.21 (m,4H), 7.48 (m,6H), 7.52 (d,2H), 7.60 (d,1H), 8.00 (s,1H)

Synthesis Example 7: Synthesis of Compound A-7

A compound A-7 was synthesized in the same manner except that 2-tert-butoxycarbonyl-4-iodophenol synthesized by the following method was used instead of 4-iodophenol in the synthesis of the compound A-2.

(12) Synthesis of 2-tert-butoxycarbonyl-4-iodophenol

2-Carboxyl-4-iodophenol (5.00 g, 18.9 mmol) and dimethylaminopyridine (0.12 g, 0.95 mmol) were dissolved in tertiary butanol (50 mL) to obtain a solution. A solution in which 1-ethyl-3-(3-dimethylaminopropyl) carbodiimide hydrochloride (5.44 g, 28.4 mmol) was dissolved in tetrahydrofuran (25 mL) was added dropwise to the solution. After stirring the mixture at room temperature for 2 hours, oxalic acid (2.56 g, 28.4 mmol) was added, and the mixture was further stirred for 1 hour. The insoluble material was removed by filtration. Thereafter, the solvent was distilled off under reduced pressure, and the obtained residue was extracted with water and ethyl acetate. The organic phase obtained was washed with a saturated aqueous solution of sodium hydrogen carbonate and saturated saline, and dried over magnesium sulfate. After filtering the dried organic phase, the solvent was distilled off under reduced pressure, normal hexane was added to the obtained residue, and the precipitate was removed by filtration. The filtrate was distilled off under reduced pressure, and thereby crystallized 2-tert-butoxycarbonyl-4-iodophenol (2.70 g, 8.43 mmol) was obtained. The yield was 44.6%.

The results of identifying the obtained compound A-7 using $^1$H-NMR were as follows.

$^1$H-NMR (CDCl$_3$): δ=1.55 (s,9H), 2.99 (t,4H), 4.38 (t,4H), 5.17 (s,2H), 5.81 (d,2H), 6.10 (dd,2H), 6.38 (d,2H), 6.92 (d,1H), 7.21 (m,4H), 7.45 (m,6H), 7.53 (m,3H), 7.85 (s,1H)

<Synthesis of Comparative Compound B-1>
According to Synthesis Example 1 of JP2005-015406A, the following compound B-1 was synthesized as a comparative compound.
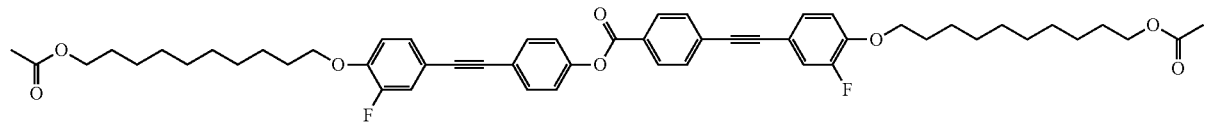 [SMILES: CC(=O)OCCCCCCCCCCOc1ccc(C#Cc2ccc(OC(=O)c3ccc(C#Cc4ccc(OCCCCCCCCCCOC(C)=O)c(F)c4)cc3)cc2)cc1F]
The compounds A-1 to A-7 and the compound B-1 are shown below.
A-1
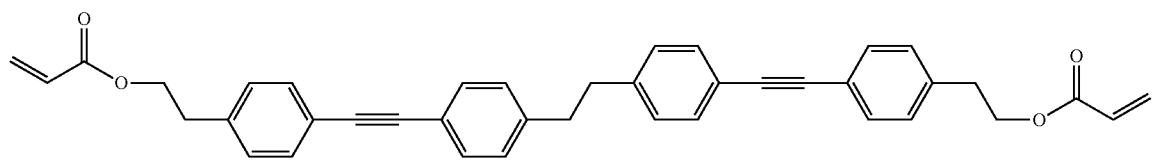
A-2
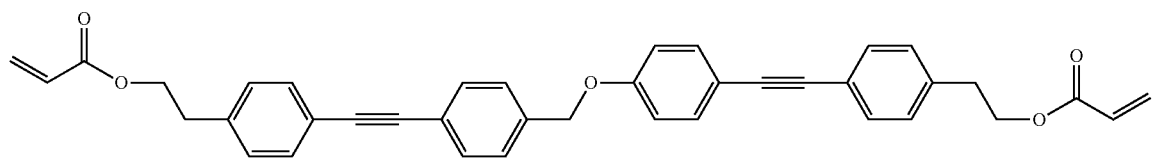
A-3
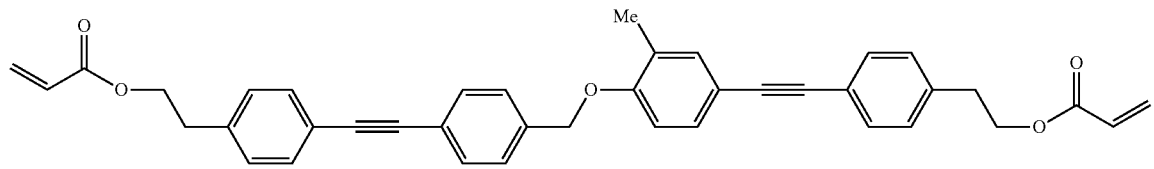
A-4
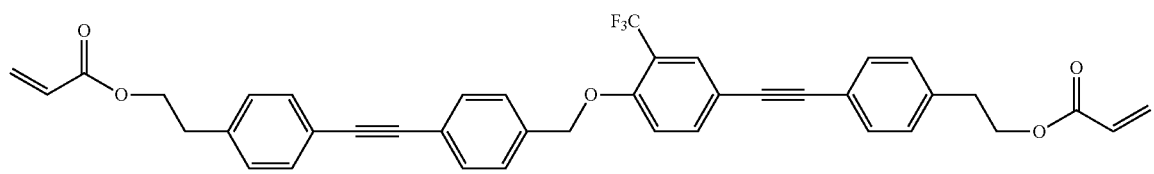
A-5
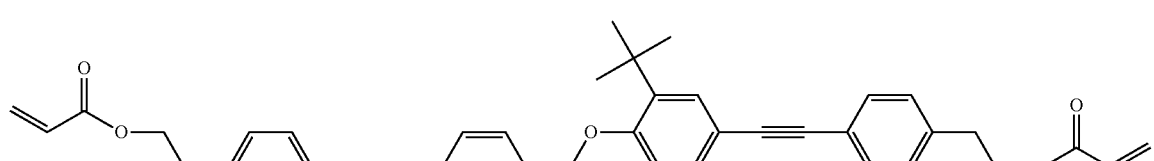
A-6
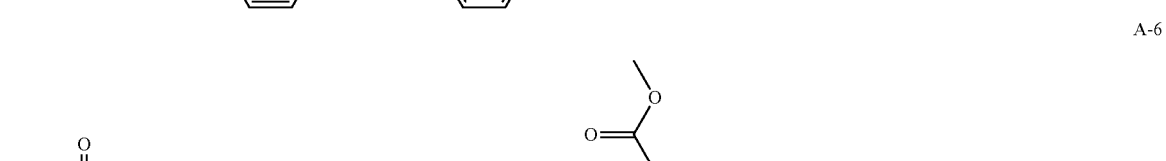

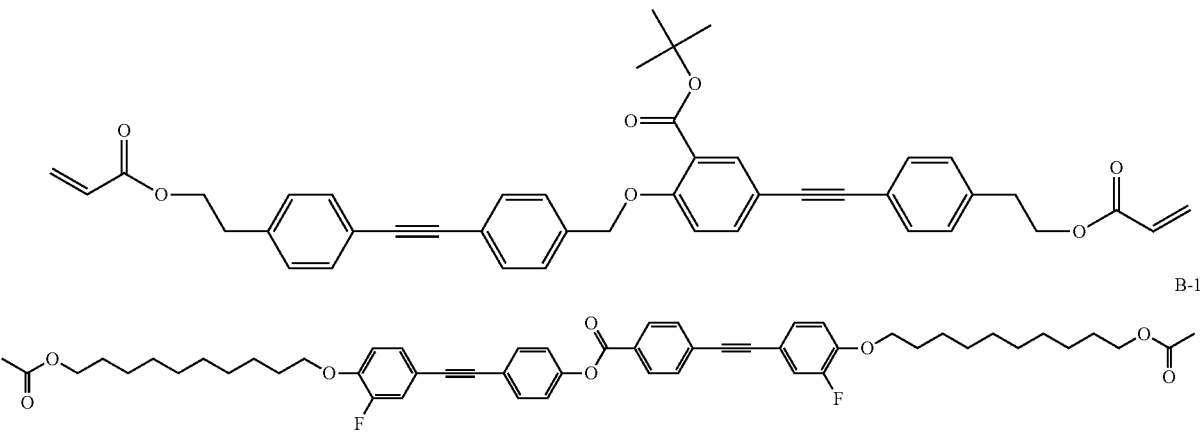

[Evaluation]

Using above-described compounds A-1 to A-7 and compound B-1, the following various evaluations were carried out.

<Phase Transition Temperature Measurement>

Each of the compounds was heated on a hot stage and observed under a polarizing microscope to investigate phase transition behavior. The results are shown in Table 1.

In the table, "Cr," "Ne," "Sc," "SA," and "Iso" respectively represent a crystalline state, a nematic phase, a smectic C phase, a smectic A phase, and an isotropic liquid.

Since A-1 and A-2 have melting points of 200° C. or higher and undergo a polymerization reaction during heating, liquid crystallinity could not be evaluated.

<Measurement of Δn (Refractive Index Anisotropy)>

Δn of each of the compounds was measured by a method using a wedge-shaped liquid crystal cell described on page 202 of the Liquid Crystal Handbook (edited by Liquid Crystal Handbook Editing Committee, published by Maruzen Co., Ltd.). In a case of the compound which is liable to crystallize, evaluation with a mixture thereof with other liquid crystals was carried out and Δn was estimated from extrapolated values thereof. The results are shown in Table 1. The values in the table represent Δn's at 550 nm and 30° C.

<Measurement of Solution Absorption Spectrum (Colorability Evaluation)>

A solution absorption spectrum of each of the compounds was measured using a spectrophotometer UV-3100PC manufactured by Shimadzu Corporation. Using chloroform as a solvent, a solution in which a predetermined amount of the compound was dissolved was measured in a 1 cm cell, and λmax and λ (1000) were calculated from the obtained spectrum and molecular weight. λmax represents a wavelength showing the maximum light absorption coefficient in the region of 300 nm or more, and λ (1000) represents a wavelength showing a light absorption coefficient ε of 1000 in the region of 300 nm or more. It can be evaluated that as wavelengths of λmax and λ (1000) became smaller (as wavelengths became shorter), colorability of the compound was more inhibited.

For example, λmax is preferably 310 nm or less. In addition, λ (1000) is preferably 350 nm or less and more preferably 325 nm or less.

<Solubility Evaluation>

Solubility of each of the compounds in methyl ethyl ketone was evaluated. A solution in which the compound was ultrasonically dissolved or dissolved by heating was produced. Thereafter, it was observed at room temperature (23° C.) whether or not the compound was precipitated in the solution. Solutions were produced at various concentrations for each of the compounds, and solubility of the compound was evaluated according to the following criteria, using a concentration at which the compound was precipitated as a precipitation concentration. As a precipitation concentration became higher, solubility of the compound was more excellent.

A: a precipitation concentration was 20% by mass or more

B: a precipitation concentration was 10% by mass or more and less than 20% by mass C: a precipitation concentration was less than 10% by mass <Light Fastness Evaluation>

(Production of Optically Anisotropic Film)

A coating liquid having the following composition was prepared and applied to a rubbing-treated glass equipped with an alignment film by spin-coating. Each composition was irradiated with ultraviolet rays of 500 mJ/cm² through a filter that cuts light having a wavelength of 350 nm or less on a hot plate heated to a temperature until showing a nematic phase, and thereby an optically anisotropic film was produced.

| Composition of coating liquid |
|---|
| Compound (A-1 to A-7 or B-1): 50 parts by mass |
| The following polymerizable liquid crystal compound (B-2): 50 parts by mass |
| The following photopolymerization initiator (P-1): 2 parts by mass |
| The following surfactant (F-1): 0.1 parts by mass |
| Chloroform: 40 parts by mass |

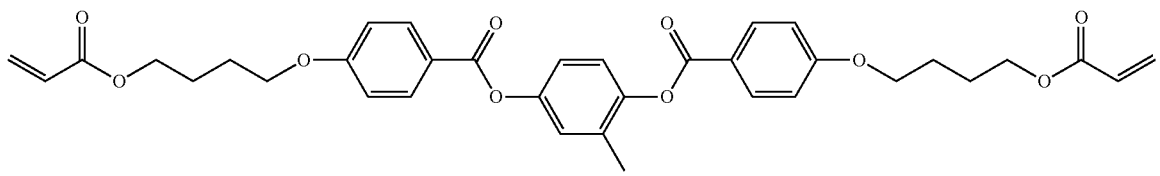

B-2

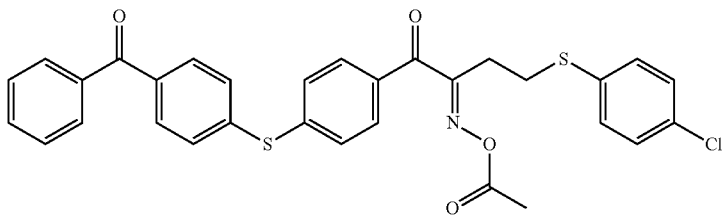

P-1

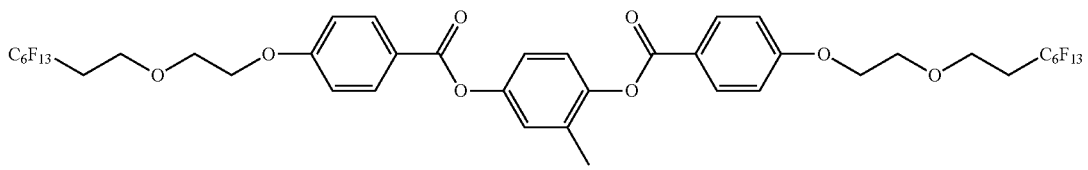

F-1

(Light Fastness Test)

The produced optically anisotropic film was irradiated with light using a Super Xenon Weather Meter SX75 manufactured by Suga Test Instruments Co., Ltd. Using KU-1000100 manufactured by King Seisakusho Co., Ltd. as a UV cut filter, a light fastness test was conducted by irradiation of 5 million lxh of light for 50 hours under an oxygen-blocking condition. A temperature of the test subject (a temperature inside the test device) was set to 63° C. A relative humidity in the test device was 50% RH.

A transmittance change of the optically anisotropic film before and after the light fastness test was measured. Light fastness in a case where a transmittance change at 420 nm was less than 5% was evaluated as A, and light fastness in a case where a transmittance change at 420 nm was 5% or more was evaluated as B. As a transmittance change became small, light fastness was more excellent.

The results are shown in the following table.

a phase transition temperature from an isotropic liquid to a nematic phase is 196° C. and a phase transition temperature from a nematic phase to a crystalline state is 88° C. during cooling.

Since A-1 and A-2 have melting points of 200° C. or higher and undergo a polymerization reaction during heating, liquid crystallinity could not be evaluated.

Δn in Comparative Example 1 is a measurement value in a nematic phase.

As shown in Table 1, it was confirmed that the compound of the present invention enables compatibility of high refractive index anisotropy Δn with inhibition of colorability (where λmax is 310 nm or less and λ (1000) is 350 nm or less). In addition, it was also confirmed that the compound of the present invention has excellent light fastness.

Furthermore, in a case where at least one of $m_1$, $m_2$, $m_3$, or $m_4$ represented an integer of 1 or more and a substituent was present in General Formula (1), it was confirmed that

TABLE 1

| | Compound | Molecular weight | Phase transition | Δn | λmax (nm) | λ (1000) (nm) | Solubility | Light fastness |
|---|---|---|---|---|---|---|---|---|
| Example 1 | A-1 | 579 | — | 0.30 | 309 | 320 | C | A |
| Example 2 | A-2 | 581 | — | 0.34 | 309 | 327 | C | A |
| Example 3 | A-3 | 595 | Cr 109(88) Ne 196 Iso | 0.34 | 308 | 327 | B | A |
| Example 4 | A-4 | 649 | Cr 117(64) Ne 150 Iso | 0.36 | 309 | 325 | A | A |
| Example 5 | A-5 | 637 | Cr 131(64) Ne 106 Iso | 0.33 | 308 | 329 | A | A |
| Example 6 | A-6 | 639 | Cr 78(61) Ne 161 Iso | 0.37 | 308 | 343 | A | A |
| Example 7 | A-7 | 681 | Cr 100(<45) Ne 118 Iso | 0.33 | 309 | 339 | A | A |
| Comparative Example 1 | B-1 | 863 | Cr 83 Sc 139 SA 203 Ne 213 Iso | 0.25 | 315 | 364 | C | B |

In Table 1, in the phase transition temperature column, numerical values in parenthesis represent crystallization temperatures during temperature lowering.

In addition, for example, "Cr 109(88) Ne 196 Iso" of the compound A-3 indicates that a phase transition temperature from a crystalline state to a nematic phase is 109° C. and a phase transition temperature from a nematic phase to an isotropic liquid is 196° C. during heating, and indicates that the compound of the present invention exhibits a wide nematic temperature range and high solubility (the results of Examples 3 to 7).

In a case where the substituent was an alkyl group having 2 or more carbon atoms or a fluoromethyl group that was an alkyl group, or an alkyloxycarbonyl group, it was confirmed that the compound of the present invention has more excellent solubility (the results of Examples 4 to 7).

In a case where Y was —C($R_{ya}$)($R_{yb}$)— in General Formula (1), it was confirmed that the compound of the present invention can further inhibit colorability (the results of Example 1).

What is claimed is:

1. A compound represented by General Formula (1):

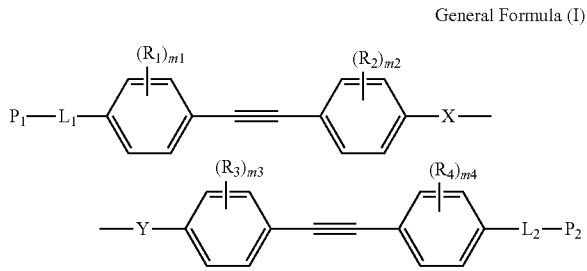

General Formula (I)

General Formula (1), $P_1$ and $P_2$ each independently represent a polymerizable group, $L_1$ and $L_2$ each independently represent a single bond or a divalent linking group, X represents —C($R_{xa}$)($R_{xb}$)—, where $R_{xa}$ and $R_{xb}$ each independently represent a hydrogen atom or a substituent, Y represents —C($R_{ya}$)($R_{yb}$)—, —O—, —$NR_{yn}$—, or —S—, where $R_{ya}$ and $R_{yb}$ each independently represent a hydrogen atom or a substituent, and $R_{yn}$ represents a hydrogen atom or an alkyl group having 1 to 6 carbon atoms, $R_1$ to $R_4$ each independently represent a substituent, $m_1$ to $m_4$ each independently represent an integer of 0 to 4, and in a case where $R_1$ to $R_4$ are each present in plurality, the $R_1$'s to $R_4$'s each may be the same as or different from each other, wherein at least one of $m_1$, $m_2$, $m_3$, or $m_4$ represents an integer of 1 or greater, at least one of $R_1$, $R_2$, $R_3$, or $R_4$ respectively matched with $m_1$, $m_2$, $m_3$, or $m_4$ each representing an integer of 1 or greater is an alkyloxycarbonyl group having 1 to 20 carbon atoms or an alkylaminocarbonyl group having 1 to 20 carbon atoms, one or more methylene groups in an alkyl group moiety in the alkyloxycarbonyl group and the alkylaminocarbonyl group each independently may be substituted by —O— or —C(=O)—, and the alkyl group moiety may have a fluorine atom.

2. The compound according to claim 1, wherein Y represents —C($R_{ya}$)($R_{yb}$)—.

3. The compound according to claim 1, wherein at least one of $m_1$, $m_2$, $m_3$, or $m_4$ represents an integer of 1 or greater.

4. The compound according to claim 1, wherein $L_1$ represents a group represented by Formula (A), and $L_2$ represents a group represented by Formula (B):

*—$Z_1$-$Sp_1$-**      Formula (A)

*—$Z_2$-$Sp_2$-**      Formula (B)

$Z_1$ and $Z_2$ each independently represent —C($R_{za}$)($R_{zb}$)—, where $R_{za}$ and $R_{zb}$ each independently represent a hydrogen atom or a substituent, $Sp_1$ and $Sp_2$ each independently represent a divalent hydrocarbon group which has 1 to 19 carbon atoms and may have a fluorine atom, or a single bond, one or more methylene groups in the divalent hydrocarbon group each independently may be substituted by —O— or —C(=O)—, and

*'s each represent a bonding position with a benzene ring group directly bonded to $L_1$ or $L_2$, and **'s each represent a bonding position with $P_1$ or $P_2$.

5. A composition comprising the compound according to claim 1.

6. The composition according to claim 5, further comprising a polymerization initiator.

7. The composition according to claim 5, further comprising a chiral agent.

8. A cured object obtained by curing the composition according to claim 5.

9. An optically anisotropic body obtained by curing the composition according to claim 5.

10. A reflective film obtained by curing the composition according to claim 5.

11. The compound according to claim 2, wherein at least one of $m_1$, $m_2$, $m_3$, or $m_4$ represents an integer of 1 or greater.

12. The compound according to claim 2, wherein $L_1$ represents a group represented by Formula (A), and $L_2$ represents a group represented by Formula (B):

*—$Z_1$-$Sp_1$-**      Formula (A)

*—$Z_2$-$Sp_2$-**      Formula (B)

$Z_1$ and $Z_2$ each independently represent —C($R_{za}$)($R_{zb}$)—, where $R_{za}$ and $R_{zb}$ each independently represent a hydrogen atom or a substituent, $Sp_1$ and $Sp_2$ each independently represent a divalent hydrocarbon group which has 1 to 19 carbon atoms and may have a fluorine atom, or a single bond, one or more methylene groups in the divalent hydrocarbon group each independently may be substituted by —O— or —C(=O)—, and

*'s each represent a bonding position with a benzene ring group directly bonded to $L_1$ or $L_2$, and **'s each represent a bonding position with $P_1$ or $P_2$.

13. A composition comprising the compound according to claim 2.

14. The composition according to claim 13, further comprising a polymerization initiator.

15. The composition according to claim 13, further comprising a chiral agent.

16. A cured object obtained by curing the composition according to claim 13.

17. An optically anisotropic body obtained by curing the composition according to claim 13.

18. A reflective film obtained by curing the composition according to claim 13.

* * * * *